(12) United States Patent
Tanaka et al.

(10) Patent No.: US 8,940,856 B2
(45) Date of Patent: Jan. 27, 2015

(54) HETEROCYCLIC COMPOUND AND HETEROCYCLIC POLYMERS

(71) Applicant: Sumitomo Chemical Company, Limited, Tokyo (JP)

(72) Inventors: Kenta Tanaka, Tsukuba (JP); Hideyuki Higashimura, Tsukuba (JP); Kazuei Ohuchi, Tsukuba (JP); Akio Tanaka, Kobe (JP); Masato Ueda, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 10 days.

(21) Appl. No.: 14/102,800

(22) Filed: Dec. 11, 2013

(65) Prior Publication Data

US 2014/0100352 A1    Apr. 10, 2014

Related U.S. Application Data

(62) Division of application No. 12/515,436, filed as application No. PCT/JP2007/072710 on Nov. 19, 2007.

(30) Foreign Application Priority Data

Nov. 22, 2006 (JP) ................................ 2006-315310
Apr. 27, 2007 (JP) ................................ 2007-118644

(51) Int. Cl.
| | | |
|---|---|---|
| C08G 75/00 | (2006.01) | |
| C08G 75/32 | (2006.01) | |
| C07D 277/20 | (2006.01) | |
| C07D 277/32 | (2006.01) | |
| C08G 61/12 | (2006.01) | |
| H01B 1/12 | (2006.01) | |
| H01L 51/00 | (2006.01) | |

(52) U.S. Cl.
CPC ............. *C08G 75/32* (2013.01); *C07D 277/20* (2013.01); *C07D 277/32* (2013.01); *C08G 61/123* (2013.01); *H01B 1/127* (2013.01); *H01L 51/0036* (2013.01); *H01L 51/0094* (2013.01)
USPC ........................... 528/377; 548/202; 526/257

(58) Field of Classification Search
USPC ............................ 528/377; 548/202; 526/257
See application file for complete search history.

(56) References Cited

U.S. PATENT DOCUMENTS

2008/0251784 A1    10/2008    Tanaka et al.

FOREIGN PATENT DOCUMENTS

| EP | 1710266 | 10/2006 |
|---|---|---|
| JP | S63250385 A | 10/1988 |
| JP | 2005-223238 A | 8/2005 |
| JP | 2005-223239 A | 8/2005 |
| JP | 2006-060116 A | 3/2006 |
| JP | 2008291229 A | 12/2008 |
| WO | 2005/070994 A1 | 8/2005 |

OTHER PUBLICATIONS

T. Chen et al., Regiocontrolled Synthesis of Poly (3-alkylthiophenes) Mediated by Rieke Zinc: Their Characterization and Solid-Stae Properties, Journal of the American Chemical Society, 1995, vol. 117, No. 1, pp. 233-244.
G. Bidan et al., Synthesis and UV-Visible Properties of Soluble Regioregular Oligo (3-octylthiophenes), Monomer to Hexamer, Chemistry of Materials, 1998, vol. 10, No. 4, pp. 1052-1058.
R.S. Loewe et al., Regioregular, Head-to-Tail coupled Poly (3-alkylthiophenes) Made Easy by the GRIM Method: Investigation of the Reaction and the Origin of Regioselectivity, Macromolecules, 2001, vol. 34, No. 13, pp. 4324-4333.
P. Stanetty et al., Halogenated 2'-Chlorobithiazoles via Pd-Catalyzed Cross-Coupling Reactions, Journal of Organic Chemistry, 2006, vol. 71, No. 10, pp. 3754-3761.
C. Boga et al., Tetrahalomethanes: simple reagents for the synthesis of monohalogenated and mixed dihalogenated aromatic heterocycles via metal-halogen exchange from lithium compounds, Journal of Organometallic Chemistry, 2000, vol. 601, No. 2, pp. 233-236.
K.J. Hodgetts et al., Regiocontrolled Synthesis of Substituted Thiazoles, Organic Letters, 2002, vol. 4, No. 8, pp. 1363-1365.
K.J. Hodgetts et al., Ethyl 2-Chlorooxazole-4-carboxylate: A Versatile Intermediate for the Synthesis of Substituted Oxazoles, Organic Letters, 2002, vol. 4, No. 17, pp. 2905-2907.

(Continued)

*Primary Examiner* — Shane Fang
(74) *Attorney, Agent, or Firm* — Sughrue Mion, PLLC

(57) ABSTRACT

The present invention provides a heterocyclic compound of the following general formula (I):

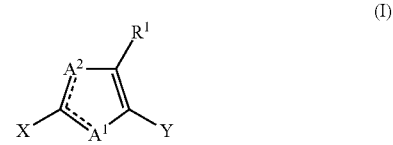

(I)

wherein X and Y are different from each other and represent a halogen atom selected from among a chlorine atom, bromine atom and iodine atom, or $CF_3SO_3^-$, $CH_3SO_3^-$, $C_6H_5SO_3^-$ or $CH_3C_6H_4SO_3^-$; $R^1$ represents an optionally substituted monovalent aliphatic hydrocarbon group having two or more carbon atoms; one of $A^1$ and $A^2$ represents —S—, —O—, —Se— or Te—, while the other represents —N=, —P= or —Si($R^2$)=, wherein $R^2$ represents a hydrogen atom, an optionally substituted monovalent hydrocarbon group, a halogen atom, an amino group or a carbonyl group; and one of two linkages each represented by a solid line and a dashed line is a single bond, while the other is a double bond.

3 Claims, No Drawings

(56) References Cited

OTHER PUBLICATIONS

J.F. Okonya et al., Synthesis of 2, 5-dihalothiazole-4-carboxylates, Tetrahedron Letters, 2002, vol. 43, No. 39, pp. 7051-7053.

T. Yokozawa and A. Yokoyama, "Chain-Growth Polycondensation: Living Polymerization Nature in Polycondensation and Approach to Condensation Polymer Architecture," Polymer Journal, vol. 36, No. 2, 2004, pp. 65-83.

M. Ng and L. Yu, "Synthesis of Amphiphilic Conjugated Diblock Oligomers as Molecular Diodes," Angew. Chem. Int. Ed., vol. 41, No. 19, 2002, pp. 3598-3601.

Office Action for Chinese Application No. 200780042955.1 dated Jun. 17, 2011.

European Patent Office, "Communication with Extended European Search Report," issued in connection with European Patent Application No. 07832435.7, dated Jan. 4, 2012.

European Patent Office, " Communication Pursuant to Rules 70(2) and 70a(2) EPC," issued in connection with European Patent Application No. 07832435.7, dated Jan. 23, 2012.

Japanese Patent Office, "Notice of Reasons for Rejection," issued in connection with Japanese Patent Application No. 2007-118644, dated Aug. 21, 2012.

Japanese Patent Office, "Decision of Rejection," issued in connection with Japanese Patent Application No. 2007-118644, dated Mar. 19, 2013.

Japanese Patent Office, "Notice of Reasons for Rejection," issued in connection with Japanese Patent Application No. 2008-107626, dated Nov. 6, 2012.

Database CA (Online) Chemical Abstracts Service, Columbus, Ohio, US, 1989, Kato et al., "Preparation of Halogenated Heterocydes as Intermediates for Agrochemicals and Drugs," XP002632769, retrieved from STN Database accession No. 1989:553776, the Abstract and the compound with the Registry-Number?: [120258-44-8] and JP 63 250385 A (Tokuyama Soda Co. Ltd., Japan) Oct. 18, 1988 (Oct. 18, 1988) the whole document.

Yamamoto et al., "p-Conjugated and Light Emitting Poly(4,4'-dialkyl-2,2'-bithiazole-5,5'-diyl)s and Their Analogues Comprised of Electron-Accepting Five-Membered Rings. Preparation, Radioregular Structure, Face-to-Face Stacking, and Electrochemical and Optical Properties," Chem. Mater., vol. 9, 1997, pp. 1217-1225.

Gan et al., "Facile Synthesis, Electronic and Optical Properties of Radioregular Head-to-Tail Oligothiazoles," Polymeric Materials: Science and Engineering, vol. 96, 2007, pp. 885-886.

Database CA (Online) Chemical Abstracts Service, Columbus, Ohio, US, 2008, Tanaka et al., "Heterocyclic Polymers with High Head-to-Tail Selectivity, Their Manufacture, Electronic Devices, and Organic Transistors," XP00263770, retrieved from STN Database accession No. 2008:1459241, abstract.

Yamamoto et al. (Marcomolecules 2003, 36, 7986-7993).

Holzweber et al. (Synlett, 2007, 19, 3016-3018).

HETEROCYCLIC COMPOUND AND HETEROCYCLIC POLYMERS

CROSS-REFERENCE TO RELATED APPLICATIONS

This is a Divisional Application of U.S. application Ser. No. 12/515,436 filed May 19, 2009 which is a National Stage of Application of PCT/JP2007/072710 filed Nov. 19, 2007, which claims priority from Japanese Patent Application Nos. 2006-315310 and 2007-118644, filed Nov. 22, 2006 and Apr. 27, 2007, respectively.

TECHNICAL FIELD

The present invention relates to a novel heterocyclic compound and heterocyclic polymer (macromolecule).

BACKGROUND ART

Conjugated polymers having as a repeating unit a structure containing a 5-membered heterocyclic ring are important as organic electronic materials. Among them, polymers having a high proportion of head to tail structure (hereinafter, referred to as "HT structure") in which the orientation of the bonds of a repeating unit are constant (hereinafter, referred to as "HT regioregular") are called "HT regioregular polymer". HT regioregular polymers are known to have high electric conductivity since flatness is higher and conjugation length is longer as compared with regiorandom polymers having a small proportion of HT structure. For example, there is suggested a HT regioregular polythiophene in which the orientation of a repeating unit is fixed at the bond position of a side chain substituent (Polymer Journal, vol. 6, p. 65 (2004)).

However, HT regioregular polymers having as a repeating unit a 5-membered ring of asymmetric ring structure are scarcely known. For example, a HT regioregular oligomer of oxazole is suggested (JP-A No. 2005-223238).

However, oligomers are believed to have poor practical utility.

Then, there is desired a compound with which a HT regioregular polymer can be synthesized having a high proportion of a HT structure having as a repeating unit a 5-membered ring of asymmetric ring structure.

Thus, the present invention has an object of providing a compound with which a HT regioregular polymer can be synthesized having as a repeating unit a 5-membered ring of asymmetric ring structure and having a high proportion of HT structure.

The present inventors have intensively studied to accomplish the above-described object and resultantly found a novel heterocyclic compound, and finally have completed the present inventions.

DISCLOSURE OF THE INVENTION

That is, the present invention provides a heterocyclic compound of the following general formula (I):

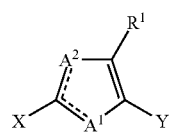
(I)

wherein X and Y are different from each other and represent a halogen atom selected from among a chlorine atom, a bromine atom and an iodine atom, or $CF_3SO_3^-$, $CH_3SO_3^-$, $C_6H_5SO_3^-$ or $CH_3C_6H_4SO_3^-$; $R^1$ represents an optionally substituted monovalent aliphatic hydrocarbon group having two or more carbon atoms; one of $A^1$ and $A^2$ represents —S—, —O—, —Se— or Te—, while the other represents —N=, —P= or —Si($R^2$)=, wherein $R^2$ represents a hydrogen atom, an optionally substituted monovalent hydrocarbon group, a halogen atom, an amino group or a carbonyl group; and one of two linkages each represented by a solid line and a dashed line is a single bond, while the other is a double bond.

The present invention provides, secondly, a method of producing the above-described heterocyclic compound comprising a step of halogenating a compound of the following general formula (III):

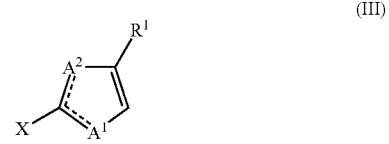
(III)

wherein X, $R^1$, $A^1$, $A^2$ and solid lines and dashed lines represent the same meanings as described above.

Further, the present invention provides a polymer having a repeating unit of the following formula (IV):

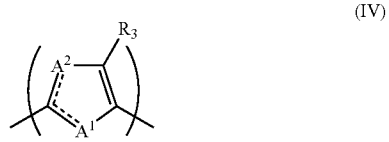
(IV)

wherein $R^3$ represents a substituent; one of $A^1$ and $A^2$ represents —S—, —O—, —Se— or Te—, while represents —N=, —P= or —Si($R^2$)=,
wherein $R^2$ represents a hydrogen atom or an optionally substituted hydrocarbon group; and one of two linkages each represented by a solid line and a dashed line is a single bond, while the other is a double bond and, wherein (A) the polymer has a structure containing consecutively connected 7 or more of the repeating units (Condition A), and (B) the proportion of the total number of direct bonds forming a head to tail (HT) bond with respect to the total number of direct bonds between the plurality of repeating units contained in the polymer is 60% or more (Condition B).

The present invention further provides a method of producing the above-described polymer comprising condensing a heterocyclic compound of the following formula (V):

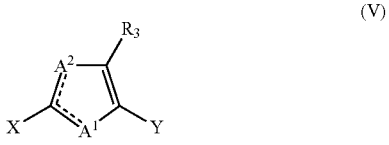
(V)

wherein X, Y, $R^3$, $A^1$, $A^2$ and solid lines and dashed lines represent the same meanings as described above.

BEST MODES FOR CARRYING OUT THE INVENTION

Next, the present invention will be illustrated in detail.
<Heterocyclic Compound>

The heterocyclic compound of the present invention is represented by the above-described general formula (I).

In the above-described general formula (I), X and Y are preferably a halogen atom selected from among a chlorine atom, a bromine atom or an iodine atom. X and Y are different, and the combination of X and Y is preferably, in no particular order, a combination of a chlorine atom and a bromine atom, a combination of a chlorine atom and an iodine atom, or a combination of a bromine atom and an iodine atom, and more specifically, when represented by (X, Y), further preferably (chlorine atom, bromine atom), (chlorine atom, iodine atom) or (bromine atom, iodine atom).

In the above-described general formula (I), the monovalent aliphatic hydrocarbon group represented by $R^1$ includes alicyclic hydrocarbon groups, and has a carbon number of preferably 2 to 16, more preferably 2 to 12, further preferably 2 to 8. Examples of the monovalent aliphatic hydrocarbon group represented by $R^1$ include alkyl groups, alkenyl groups, alkynyl groups and the like. Specific examples of the alkyl group include an ethyl group, a n-propyl group, an isopropyl group, a cyclopropyl group, a n-butyl group, an isobutyl group, a t-butyl group, a cyclobutyl group, a pentyl group, an isopentyl group, a neopentyl group, a cyclopentyl group, a hexyl group, a cyclohexyl group, a methylcyclohexyl group, a menthyl group, a pinanyl group, a bicycloheptyl group (namely, a norbornyl group), an octyl group, a nonyl group, a decyl group, an undecyl group, a dodecyl group and the like. Specific examples of the alkenyl group include a vinyl group, a n-propenyl group, an isopropenyl group, a cyclopropenyl group, a n-butenyl group, an isobutenyl group, cyclobutenyl group, a pentenyl group, an isopentenyl group, a cyclopentenyl group, a hexenyl group, a cyclohexenyl group, a methylcyclohexenyl group, a cyclohexenyl group, a cyclohexadienyl group, an octenyl group, a nonenyl group, a decenyl group, an undecenyl group, a dodecenyl group and the like. Specific examples of the alkynyl group include an acetyl group, a n-propynyl group, a cyclopropynyl group, a n-butynyl group, n-butynl group, a pentynyl group, an isopentynyl group, a cyclopentynyl group, a hexynyl group, a cyclohexynyl group, a methylcyclohexynyl group, a cyclohexynyl group, an octynyl group a nonynyl group, a decynyl group, an undecynyl group, a dodecynyl group and the like, preferably alkyl groups having 2 to 16 carbon atoms, more preferably alkyl groups having 2 to 12 carbon atoms, further preferably alkyl groups having 2 to 8 carbon atoms. These carbon numbers do not include the carbon number of substituents described later.

A part of or all of hydrogen atoms in the monovalent aliphatic hydrocarbon group represented by $R^1$ may be substituted by substituent(s). The above-described substituent includes a halogen atom, an amino group, a nitro group, a sulfonyl group, a phosphonyl group, a thiol group, an alkoxy group having 1 to 20 carbon atoms, a hydroxyl group, an alkyl group having 1 to 20 carbon atoms, an alkoxycarbonyl group having 1 to 20 carbon atoms, an alkylcarbonyloxy group having 1 to 20 carbon atoms, an alkylcarbonyl group having 1 to 20 carbon atoms, an aldehyde group and the like. As specific examples of the alkyl group, a methyl group is mentioned in addition to the examples of the above-described alkyl group. Specific examples of the alkoxy group include a methoxy group, an ethoxy group, a n-propyloxy group, an isopropyloxy group, a cyclopropyloxy group, a n-butyloxy group, an isobutyloxy group, a t-butyloxy group, a cyclobutyloxy group, a pentyloxy group, an isopentyloxy group, a neopentyloxy group, a cyclopentyloxy group, a hexyloxy group, a cyclohexyloxy group, a methylcyclohexyloxy group, a cyclohexenyloxy group, a cyclohexadienyloxy group, a menthyloxy group, a pinanyloxy group, a bicycloheptyloxy group (namely, a norbornyloxy group), an octyloxy group, a nonyloxy group, a decyloxy group, an undecyloxy group, a dodecyloxy group, a xylyloxy group, a mesityloxy group, a cumyloxy group and the like. Specific examples of the aryl group include a phenyl group, a 1-naphthyl group, a 2-naphthyl group and the like. Specific examples of the aralkyl group include a 1-phenylethyl group, a 2-phenylethyl group, a 2-methylphenyl group, a 3-methylphenyl group, a 4-methylphenyl group, a benzyl group, a xylyl group, a mesityl group, a cumyl group and the like. As the above-described alkyloxycarbonyl group, an alkylcarbonyloxy group and an alkylcarbonyl group, groups obtained by binding an oxycarbonyl group, carbonyloxy group and carbonyl group, respectively, to the above-described alkyl groups (including a methyl group) are mentioned.

In the above-described general formula (I), one of $A^1$ and $A^2$ represents —S—, —O—, —Se— or Te—, while the other represents —N=, —P= or —Si($R^2$)=, wherein $R^2$ represents a hydrogen atom, an optionally substituted monovalent hydrocarbon group, a halogen atom, an amino group or a carbonyl group. Examples of the combination of $A^1$ and $A^2$ include, in no particular order, a combination of —S— and —N=, a combination of —O— and —N=, a combination of —Se— and —N=, a combination of —S— and —P=, a combination of —O— and —P=, a combination of —Se— and —P=, a combination of —S— and —Si($R^2$)=, a combination of —O— and —Si($R^2$)=, a combination of —Se— and —Si($R^2$)=, and the like, and more specifically, when represented by ($A^1$, $A^2$), include preferably (—S—, —N=), (—O—, —N=), (—Se—, —N=), (—S—, —P=), (—O—, —P=), (—Se—, —P=), (—S—, —Si($R^2$)=), (—O—, —Si($R^2$)=) and (—Se—, —Si($R^2$)=), more preferably (—S—, —N=), (—O—, —N=), (—Se—, —N=), (—S—, —Si($R^2$)=) and (—O—, —Si($R^2$)=), further preferably (—S—, —N=).

As the optionally substituted monovalent hydrocarbon group represented by $R^2$ in the above-described general formula (I), a methyl group is mentioned in addition to those explained and shown in the above-described paragraph of the monovalent aliphatic hydrocarbon group. $R^2$ represent preferably a hydrogen atom or an alkyl group having 1 to 12 carbon atoms, more preferably a hydrogen atom or an alkyl group having 1 to 6 carbon atoms, further preferably a hydrogen atom.

A part of or all of hydrogen atoms in the optionally substituted monovalent hydrocarbon group represented by $R^2$ may be substituted by substituent(s). The substituent includes a halogen atoms, an amino group, a nitro group, a sulfonyl group, a phosphonyl group, a thiol group, an alkoxy group having 1 to 20 carbon atoms, an aralkyloxy group having 1 to 20 carbon atoms, an aryloxy group having 1 to 20 carbon atoms, a hydroxyl group, an alkyl group having 1 to 20 carbon atoms, an aryl group having 6 to 20 carbon atoms, an aralkyl group having 7 to 20 carbon atoms, an alkyloxycarbonyl group having 1 to 20 carbon atoms, an alkylcarbonyloxy group having 1 to 20 carbon atoms, an alkylcarbonyl group having 1 to 20 carbon atoms, an aldehyde group and the like. Specific examples of the alkoxy group include a methoxy group, an ethoxy group, a n-propyloxy group, an isopropyloxy group, a cyclopropyloxy group, a n-butyloxy group, an isobutyloxy group, a t-butyloxy group, a cyclobutyloxy group, a pentyloxy group, an isopentyloxy group, a neopentyloxy group, a cyclopentyloxy group, a hexyloxy group, a cyclohexyloxy group, a methylcyclohexyloxy group, a cyclohexenyloxy group, a cyclohexadienyloxy group, a menthyloxy group, a pinanyloxy group, a bicycloheptyloxy group (namely, a norbornyloxy group), an octyloxy group, a nonyloxy group, a decyloxy group, an undecyloxy group, a dodecyloxy group and the like. Specific examples of the aralkyloxy group include a 1-phenylethoxy group, a 2-phenylethyloxy group, a 2-methylphenyloxy group, a 3-methylphenyloxy group, a 4-methylphenyloxy group, a benzyloxy group and the like. Specific examples of the aryloxy group include a phenyloxy group, a xylyloxy group, a mesityloxy group, a cumyloxy group, a 1-naphthyloxy group, a 2-naphthyloxy group and the like. Specific examples of the alkyl group include a methyl group, an ethyl group, a n-propyl group, an isopropyl group, a cyclopropyl group, a n-butyl group, an isobutyl group, a t-butyl group, a cyclobutyl group, a pentyl group, an isopentyl group, a neopentyl group, a cyclopentyl group, a hexyl group, a cyclohexyl group, a methylcyclohexyl group, a cyclohexenyl group, a cyclohexadienyl group, a menthyl group, a pinanyl group, a bicycloheptyl group (namely, a norbornyl group), an octyl group, a nonyl group, a decyl group, an undecyl group and a dodecyl group. Specific examples of the aralkyl group include a 1-phenylethyl group, a 2-phenylethyl group, a 2-methylphenyl group, a 3-methylphenyl group, a 4-methylphenyl group, a benzyl group and the like. Specific examples of the aryl group include a phenyl group, a xylyl group, a mesityl group, a cumyl group, a 1-naphthyl group, a 2-naphthyl group and the like. As the above-described alkyloxycarbonyl group, an alkylcarbonyloxy group and an alkylcarbonyl group, groups obtained by binding an oxycarbonyl group, a carbonyloxy group and a carbonyl group, respectively, to the above-described alkyl groups are mentioned.

Preferable are heterocyclic compounds of the present invention of the above-described general formula (I) in which X and Y are different each other and represent a chlorine atom, a bromine atom or an iodine atom, and one of $A^1$ and $A^2$ is —S— or —O—, while the other is —N=.

As specific examples of the heterocyclic compound of the present invention, those represented by the following structural formulae are mentioned.

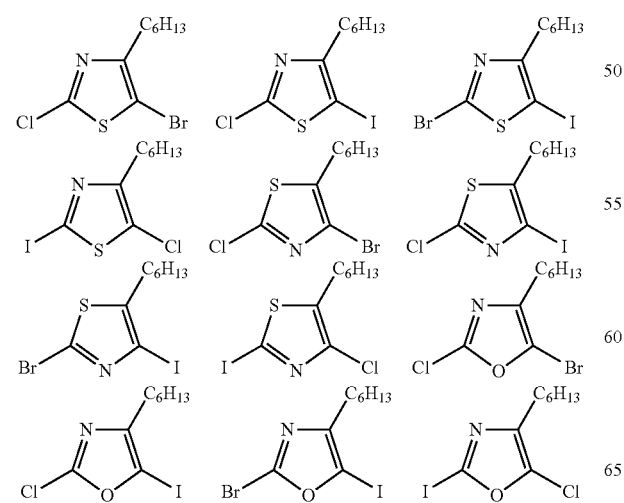

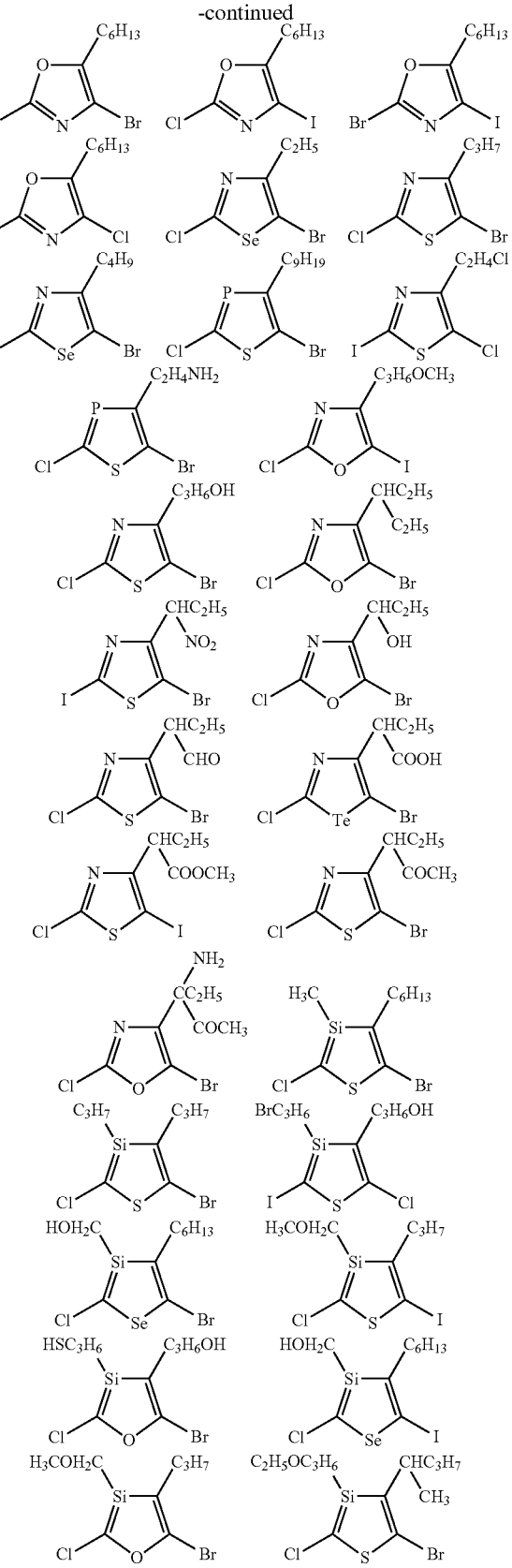

Among them, those represented by the following structural formulae are preferable from the standpoint of solubility.

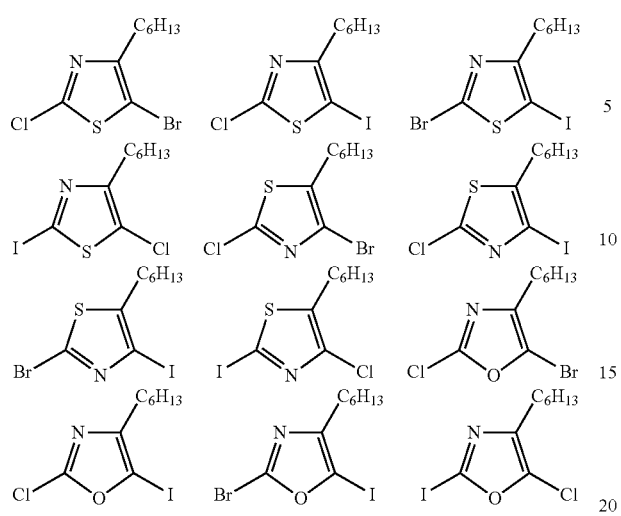

Those represented by the following structural formulae are further preferable from the standpoint of easiness of synthesis.

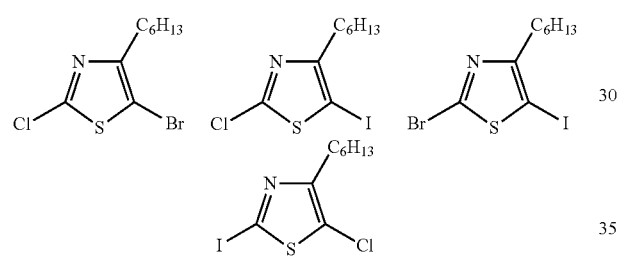

—Production Method—

The heterocyclic compound of the present invention may be synthesized by any methods, and it is preferable that the heterocyclic compound is synthesized from a heterocyclic compound of the following general formula (II):

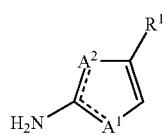

(II)

wherein $R^1$, $A^1$, $A^2$, and two parallel lines composed of solid lines and dashed lines have the same meanings as described above, by a method including the following first step and/or second step, preferably a method including the following first step and second step, from the standpoint of purity thereof and synthesis efficiency. The two-stage reaction will be illustrated in detail below.

The first step is a step of releasing an amino group from an amine compound of the above-described general formula (II) and adding a halogen atom, to synthesize a compound of the above-described general formula (III).

The second step is a step of halogenating a compound of the above-described general formula (III).

The halogenation is preferably carried out with halogen gas and/or N-halogenosuccinimide.

Other steps may be provided before or after these first or second steps.

Next, referring to the synthesis of a thiazole compound of the following structural formula (Ia):

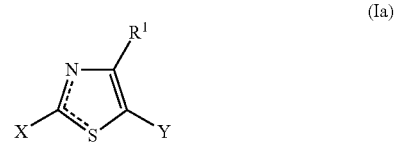

(Ia)

wherein X, Y, $R^1$ and solid lines and dashed lines represent the same meanings as described above, as one example, the above-described first step and second step will be illustrated specifically.

In the first step, an amine compound of the following general formula (IIa):

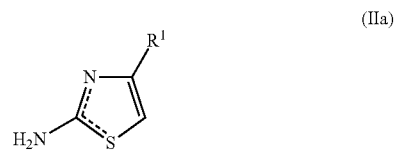

(IIa)

wherein, $R^1$ and solid lines and dashed lines represent the same meanings as described above, can be stirred, for example, with (1) an alkyl nitrite and (2) a hydrogen halide or a metal halide, continuously or simultaneously, to release amino group and add a halogen atom, thereby synthesizing a compound of the following general formula (IIIa):

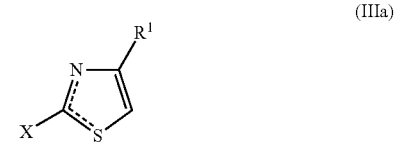

(IIIa)

wherein X, $R^1$ and solid lines and dashed lines represent the same meanings as described above.

The use amount of the alkyl nitrite is usually 1 to 2 mol, preferably 1 to 1.3 mol with respect to 1 mol of the above-described amine compound.

The use amount of the hydrogen halide or metal halide is usually 1 to 5 mol, preferably 1 to 3 mol with respect to 1 mol of the above-described amine compound.

In the second step, thus obtained compound can be halogenated with halogen gas (for example, chlorine gas and the like) and/or N-halogenosuccinimide (for example, N-bromosuccinimide and the like) to synthesize an intended thiazole compound. The total use amount of the above-described halogen gas and N-halogenosuccinimide is usually 1 to 10 mol, preferably 1 to 1 mol with respect to 1 mol of the above-described compound.

A specific scheme of the above-described synthesis method is, for example, as described below,

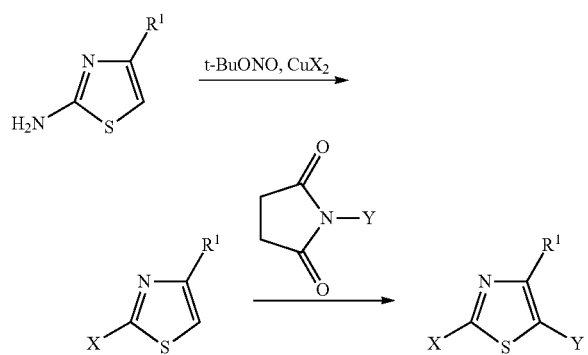

wherein X, Y and $R^1$ represent the same meanings as described above.

—Synthesis of HT Regioregular Polymer—

When a heterocyclic compound of the present invention and methylmagnesium chloride are stirred in the presence of a solvent, either a halogen atom X or Y in the above-described heterocyclic compound reacts selectively, and then, if a suitable catalyst (for example, 1,3-diphenylphosphinopropanenickel(II) chloride (Ni(dppp)Cl$_2$) and the like) is added to the reaction liquid, polymerization occurs to obtain a HT regioregular polymer. Utilizing the difference of such reactivity (selectivity), only one regioisomer based on the above-described heterocyclic compound as a substrate can be obtained selectively.

<Polymer>

The polymer of the present invention contains a repeating unit of the above-described formula (IV) and is characterized in that the above-described Conditions (A) and (B) are satisfied.

Examples of the substituent represented by $R^3$ in the above-described formula (IV) include an optionally substituted hydrocarbon group, an optionally substituted alkoxy group, an optionally substituted di(hydrocarbyl)amino group, an optionally substituted hydrocarbylmercapto group, an optionally substituted hydrocarbylcarbonyl group, an optionally substituted hydrocarbyloxycarbonyl group, an optionally substituted di(hydrocarbyl)aminocarbonyl group, an optionally substituted hydrocarbyloxysulfonyl group and the like, preferably an optionally substituted hydrocarbon group, an optionally substituted alkoxy group, an optionally substituted di(hydrocarbyl)amino group, an optionally substituted hydrocarbylmercapto group, an optionally substituted hydrocarbylcarbonyl group and an optionally substituted hydrocarbyloxycarbonyl group, more preferably an optionally substituted hydrocarbon group, an optionally substituted alkoxy group and an optionally substituted di(hydrocarbyl)amino group, further preferably an optionally substituted hydrocarbon group and an optionally substituted alkoxy group.

Examples of the hydrocarbon group represented by $R^3$ in the above-described formula (I) include alkyl groups having about 1 to 50 carbon atoms such as a methyl group, an ethyl group, a propyl group, an isopropyl group, a butyl group, an isobutyl group, a t-butyl group, a pentyl group, a hexyl group, a nonyl group, a dodecyl group, a pentadecyl group, an octadecyl group, a docosyl group and the like; cyclic saturated hydrocarbon groups having about 3 to 50 carbon atoms such as a cyclopropyl group, a cyclobutyl group, a cyclopentyl group, a cyclohexyl group, a cyclononyl group, a cyclododecyl group, a norbornyl group, an adamantyl group and the like; alkenyl groups having about 2 to 50 carbon atoms such as an ethenyl group, a propenyl group, a 3-butenyl group, a 2-butenyl group, a 2-pentenyl group, a 2-hexenyl group, a 2-nonenyl group, a 2-dodecenyl group and the like; aryl groups having about 6 to 50 carbon atoms such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-t-butylphenyl group, a 4-hexylphenyl group, a 4-cyclohexylphenyl group, a 4-adamantylphenyl group, a 4-phenylphenyl group and the like; and aralkyl groups having about 7 to 50 carbon atoms such as a phenylmethyl group, a 1-phenyleneethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group, a 6-phenyl-1-hexyl group and the like.

The hydrocarbon group represented by $R^3$ in the above-described formula (IV) preferably has 1 to 20 carbon atoms, more preferably has 2 to 18 carbon atoms, and further preferably has 3 to 13 carbon atoms.

The alkoxy group, hydrocarbylmercapto group, hydrocarbylcarbonyl group, hydrocarbyloxycarbonyl group and hydrocarbylsulfonyl group represented by $R^3$ in the above-described formula (IV) are groups obtained by binding one of the above-described hydrocarbon groups to an oxy group, a mercapto group, a carbonyl group, an oxycarbonyl group and a sulfonyl group, respectively. These hydrocarbon groups are the same as explained and shown above.

The di(hydrocarbyl)amino group and di(hydrocarbyl)aminocarbonyl group represented by $R^3$ in the above-described (IV) are groups obtained by substituting two hydrogen atoms in an amino group and an aminocarbonyl group (namely, —C(C═O)—NH$_2$) by the above-described hydrocarbon group, respectively. These hydrocarbon groups are the same as explained and shown above.

Part of or all of hydrogen atoms contained in the hydrocarbon group, alkoxy group, di(hydrocarbyl)amino group, hydrocarbylmercapto group, hydrocarbylcarbonyl group, hydrocarbyloxycarbonyl group, di(hydrocarbyl)aminocarbonyl group, hydrocarbyloxysulfonyl group and the like represented by $R^3$ in the above-described formula (IV) may be substituted by halogen atom(s), hydroxyl group(s), aldehyde group(s), amino group(s), nitro group(s), cyano group(s), hydroxycarbonyl group(s), alkoxy group(s), hydrocarbylmercapto group(s), hydrocarbylcarbonyl group(s), hydrocarbyloxycarbonyl group(s), hydrocarbylsulfonyl group(s) and the like.

When the substituent represented by $R^3$ is an optionally substituted di(hydrocarbyl)amino group or an optionally substituted di(hydrocarbyl)aminocarbonyl group, a part of or all of hydrogen atoms bonded to a nitrogen atom are preferably substituted by a monovalent alkoxy group from the standpoint of synthesis and solubility in an organic solvent of a polymer.

In the above-described formula (IV), the same examples are mentioned also for $A^1$ and $A^2$. The combination of $A^1$ and $A^2$ includes, in no particular order, preferably a combination of —S— and —N═, a combination of —O— and —N═, a combination of —Se— and —N═, a combination of —S— and —P═, a combination of —O— and —P═, a combination of —Se— and —P═, a combination of —S— and —Si(R$^2$)═, a combination of —O— and —Si(R$^2$)═, and a combination of —Se— and —Si(R$^2$)═, more preferably a combination of —S— and —N═, a combination of —O— and —N=, a combination of —Se— and —N=, a combination of —S— and —Si(R²)=, and a combination of —O— and —O—Si(R²)=, further preferably a combination of —S— and —N=, and a combination of —O— and —N=, particularly preferably a combination of —S— and —N=.

The optionally substituted hydrocarbon group represented by R² in the above-described formula (IV) is the same as described above.

As the repeating unit of the above-described formula (IV), for example, those represented by the following structural formulae are mentioned.

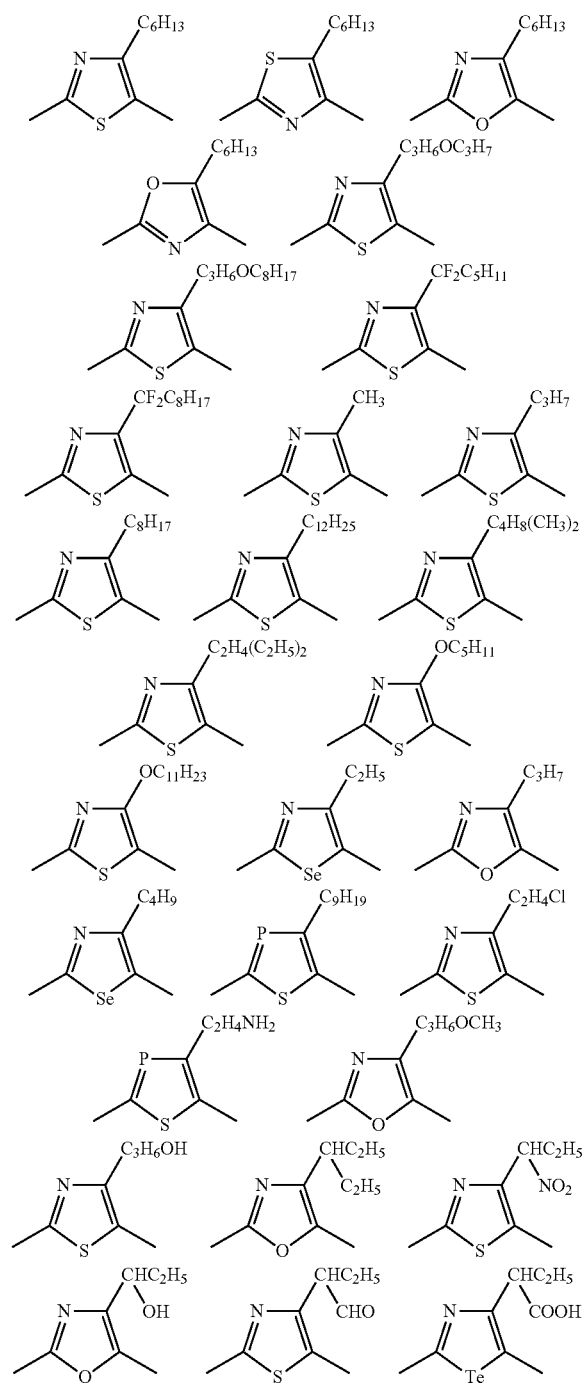
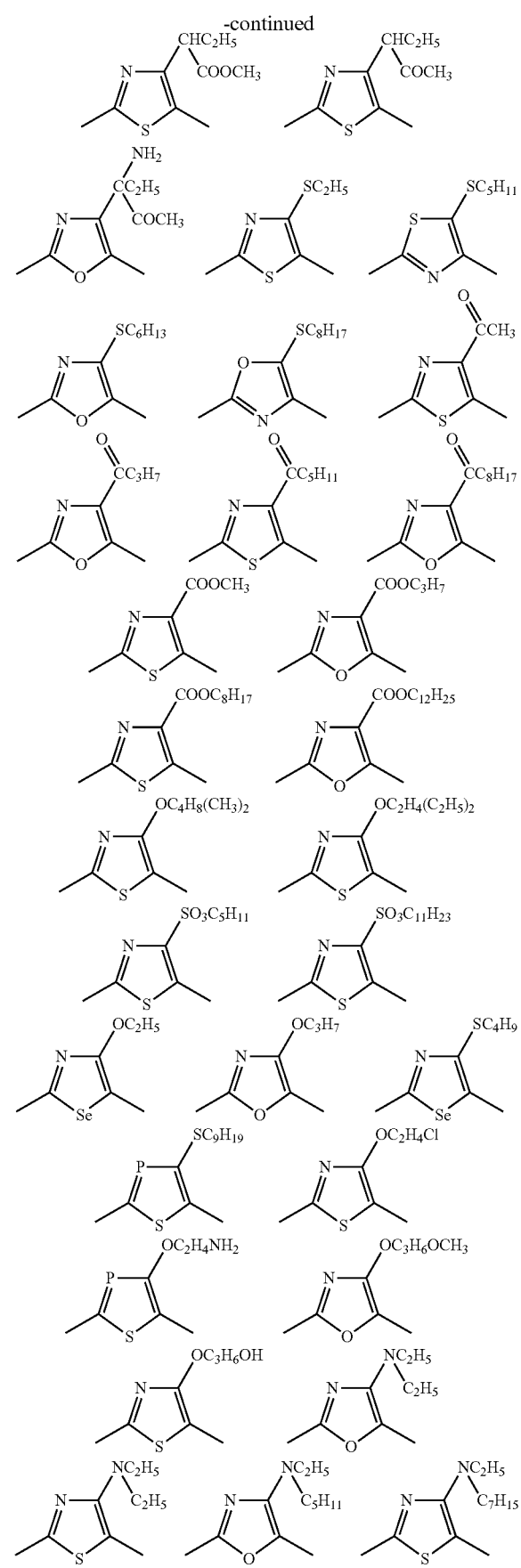

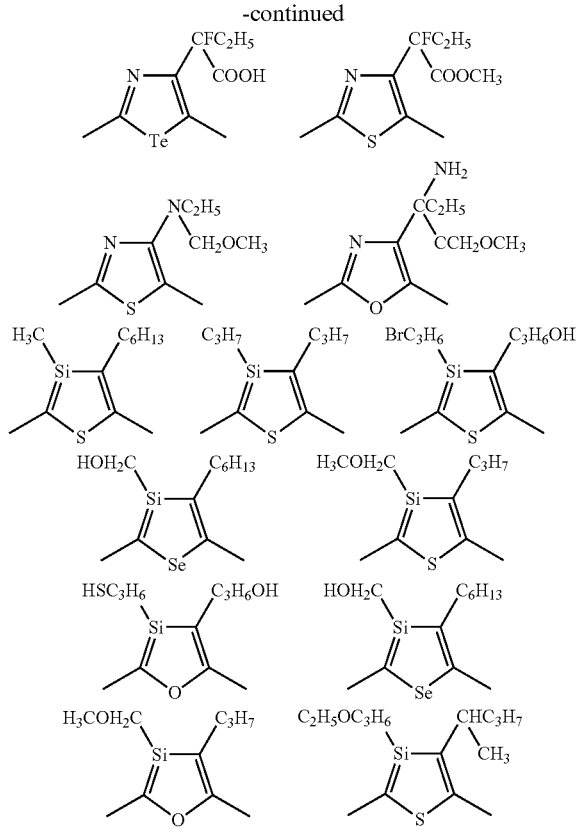

Among them, repeating units represented by the following structural formulae are preferable from the standpoint of synthesis of polymer.

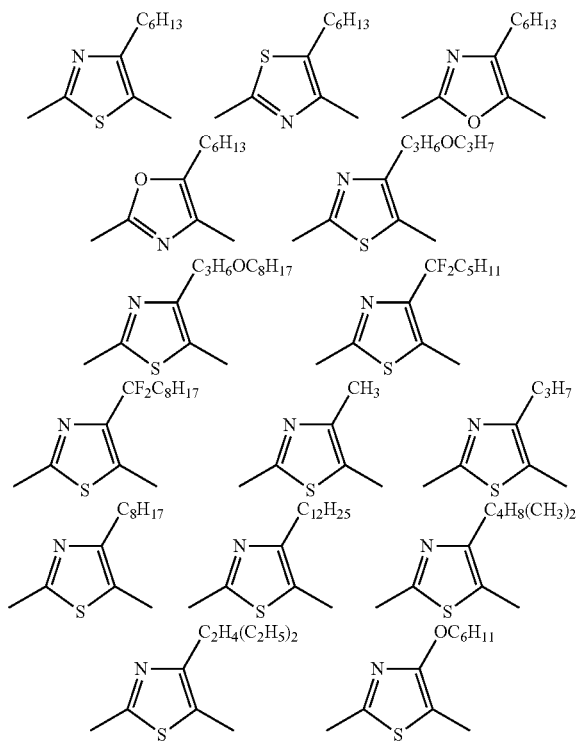

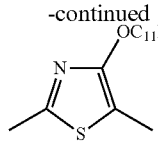

Among them, repeating units represented by the following structural formulae are more preferable from the standpoint of synthesis of polymer.

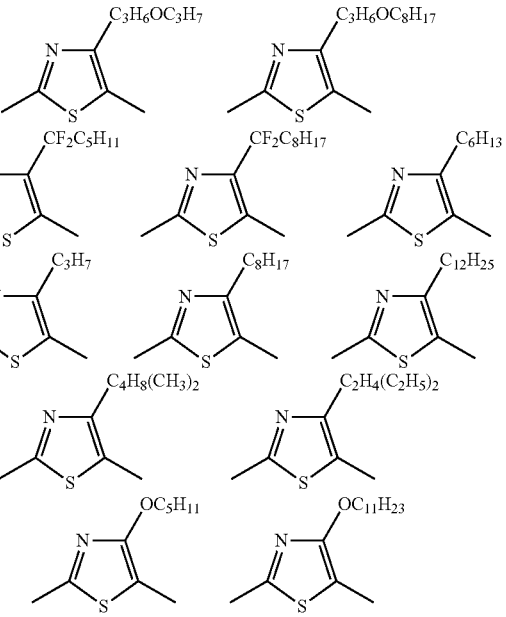

The repeating unit contained in the polymer of the present invention may be only one repeating unit of the above-described formula (IV) (namely, homopolymer) or a combination of two or more repeating units of the above-described formula (IV) (namely, copolymer), and from the standpoint of synthesis of polymer, the number of the repeating unit of the above-described formula (IV) is preferably 3 or less, more preferably 2 or less, particularly preferably 1. The polymer of the present invention may contain also other repeating units, in addition to the repeating unit of the above-described formula (IV).

When the polymer of the present invention further contains a repeating unit other than the repeating unit of the above-described formula (IV), the proportion of the total number of repeating units of the above-described formula (IV) with respect to the total number of all repeating units contained in the polymer is preferably 80% or more and less than 100%, from the standpoint of packing property between molecules, more preferably 85% or more and less than 100%, further preferably 90% or more and less than 100%, particularly preferably 94% or more and less than 100%.

In the polymer of the present invention, the number of repeating units of the above-described formula (IV) consecutively connected can be estimated by a matrix assisted laser desorption ionization mass analysis (MALDI-TOFMS) method. The polymer of the present invention has a structure in which 7 or more repeating units of the above-described formula (IV) are consecutively connected, and from the standpoint of solubility of the polymer in an organic solvent and easiness of purification thereof, a structure in which 7 to $10^6$ repeating units are consecutively connected is preferable, a structure in which 7 to $10^5$ repeating units are consecutively connected is more preferable, a structure in which 7 to $10^4$ repeating units are consecutively connected is particularly preferable.

The head to tail (HT) bond contained in the polymer of the present invention is defined as described below. When focusing on two heterocyclic rings noticed in a combination of a plurality of 5-membered heterocyclic rings like in a structure of the following formula (VI), if a carbon atom directly bonded to $A^1$ and $A^2$ (namely, a carbon atom represented by $C^{*1}$ in $-A^1-C^{*1}-A^2-$ part in the 5-membered ring) is denoted as "head (H)" and the other carbon atom directly bonded to $A^1$ (namely, a carbon atom represented by $C^{*2}$ in $-A^1-C^{*2}-C^{*3}$ ($R^1$)-$A^2$- part in the 5-membered ring) is denoted as "tail (T)", then, a direct bond (H-T) connecting "head" in one heterocyclic ring and "tail" in the other heterocyclic ring is the head to tail (H-T) bond. Since a plurality (7 or more) of repeating units of the above-described formula (IV) are present in the polymer of the present invention, the number of the HT bond is counted hypothetically that "H-T" is one.

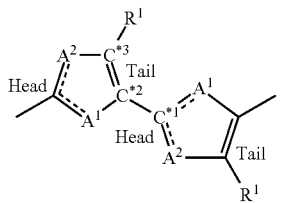
(VI)

The proportion of the total number of the direct bond forming the HT bond (hereinafter, referred to as "HT regioregularity") with respect to the total number of direct bonds (specifically, H—H bond, T-T bond, H-T can be applied) between a plurality of repeating units contained in the polymer is 60% or more in the polymer of the present invention, and from the standpoint of sufficiently securing the flatness of the whole polymer molecule, it is preferably 80% or more, more preferably 90% or more, particularly preferably 95% or more. The upper limit thereof is 100%. When the HT regioregularity is less than 60%, the flatness of the whole polymer molecule is poor to cause difficult flow of electricity. The HT regioregularity of the polymer of the present invention is obtained in the form of average value according to $^1$H-NMR spectrum. When it cannot be measured because of overlap of different signals in the $^1$H-NMR spectrum depending on the kind of a substituent, however, it can be obtained in the form of average value according to ultraviolet spectrum.

—Production Method—

The polymer of the present invention may be synthesized by any methods, and it is preferable that the polymer is synthesized by a method containing condensing a heterocyclic compound of the above-described formula (V) from the standpoint of purity and synthesis efficiency thereof. The heterocyclic compound of the above-described formula (V) can be synthesized by the same method as the synthesis method of a heterocyclic compound of the formula (I) described above.

Specifically, X and/or Y in the heterocyclic compound reacts selectively when a heterocyclic compound of the above-described formula (V) and a suspension of activated zinc or a Grignard reagent ($R^4MgZ$) are mixed in the presence of a solvent, then the polymerization reaction initiates by adding suitable catalyst to the mixture, and the polymer of the present invention can be obtained.

The suspension of activated zinc to be used in the above-described polymerization reaction can be purchased from Aldrich, and it is obtained in the form of THF suspension by slowly adding dropwise a THF solution of zinc chloride into a tetrahydrofuran (THF) solution of lithium and effective amount of naphthalene, in an argon flow, as shown in J. Am. Chem. Soc. vol. 117, p. 242 (1995).

In the Grignard reagent to be used in the above-described polymerization reaction, $R^4$ represents a hydrocarbon group. The hydrocarbon group represented by $R^4$ is the same as explained and shown for the hydrocarbon group represented by $R^3$. Z represents a halogen atom, specifically, a chlorine atom, a bromine atom, an iodine atom or the like.

Specific examples of the Grignard reagent include $CH_3MgCl$, $CH_3C(CH_3)_2MgCl$, $CH_3(CH_2)_3MgCl$, $CH_3MgBr$, $CH_3C(CH_3)_2MgBr$, $CH_3(CH_2)_3MgBr$, $CH_3MgI$, $CH_3C(CH_3)_2MgI$, $CH_3(CH_2)_3MgI$ and the like, preferably $CH_3MgCl$, $CH_3C(CH_3)_2MgCl$, $CH_3(CH_2)_3MgCl$, $CH_3MgBr$, $CH_3C(CH_3)_2MgBr$ and $CH_3(CH_2)_3MgBr$, further preferably $CH_3MgCl$, $CH_3C(CH_3)_2MgCl$ and $CH_3(CH_2)_3MgCl$.

Among the above-described suspension of activated zinc and Grignard reagent, the Grignard reagent is preferable from the standpoint of easy handling.

As the solvent to be used in the above-described polymerization reaction, aprotic solvents and non-polar solvents which are hard to cause side reactions are preferable, and examples thereof include aromatic hydrocarbons such as benzene, toluene, xylene and the like; linear and cyclic aliphatic hydrocarbons such as heptane, cyclohexane and the like; halogenated hydrocarbons such as chlorobenzene, dichlorobenzene, dichloromethane and the like; nitriles such as acetonitrile, benzonitrile and the like; ethers such as dioxane, THF, ethylene glycol dimethyl ether and the like; amides such as N,N-dimethylformamide, N-methylpyrrolidone and the like; nitro compounds such as nitromethane, nitrobenzene and the like. Preferable as the reaction solvent are aromatic hydrocarbons, halogenated hydrocarbons, nitriles, ethers and nitro compounds. The solvents may be used singly or in combination with two or more.

In the above-described polymerization reaction, it is preferable that when the heterocyclic compound of the above-described formula (I) and a suspension of activated zinc and Grignard reagent are mixed in the presence of the above-described solvent, X and/or Y in the heterocyclic compound selectively reacts to obtain any of the following organometal compounds selectively.

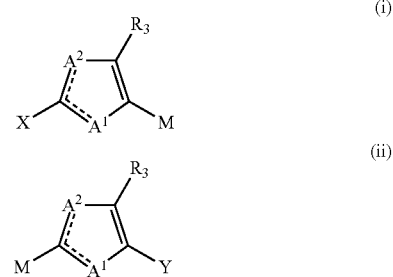

In the structures, X, Y, $R^3$, $A^1$ and $A^2$ and solid lines and dashed lines represent the same meanings as described above, and M represents MgZ or Zn, and Z represents the same meaning as described above.

Examples of suitable catalysts to be used in the above-described polymerization reaction include copper complexes, palladium complexes, nickel complexes and the like containing ligands represented by the following formulae, among complexes described in Chem. Rev. 102, 1359(2002).

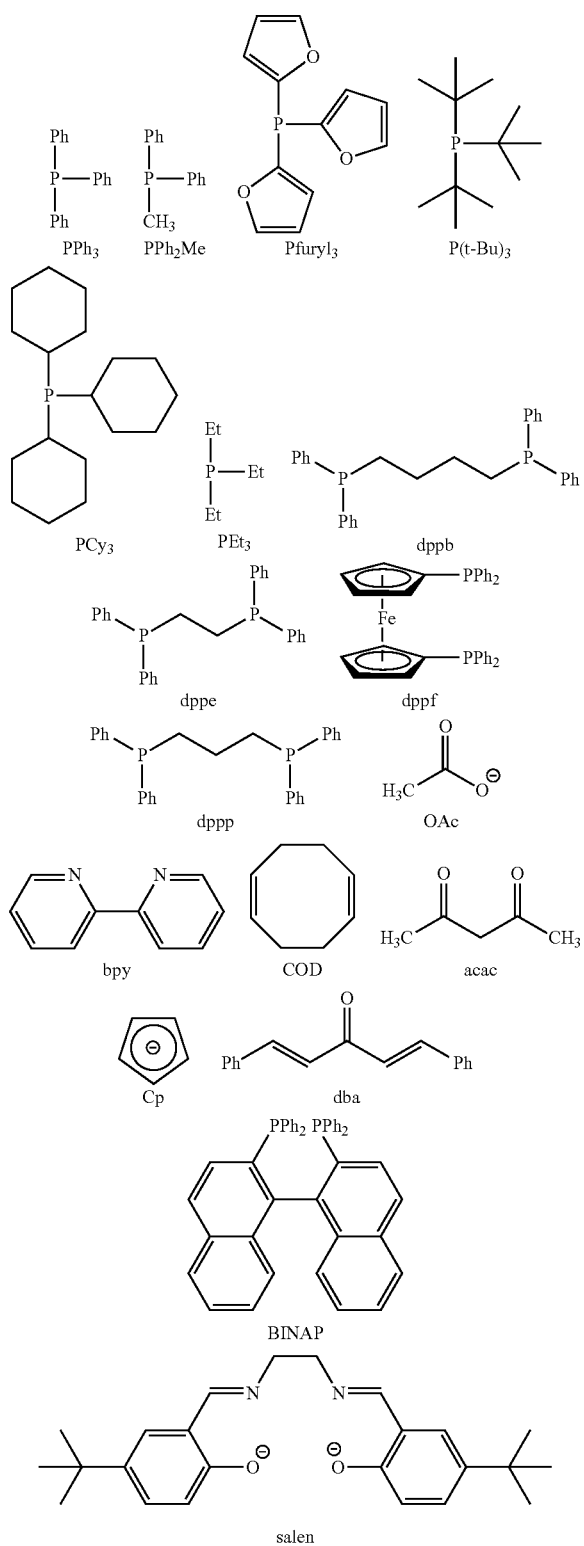

Preferable as suitable catalysts to be used in the above-described polymerization reaction are Pd(PPh$_2$Me)$_2$, Pd(P(t-Bu)$_3$)$_2$, Pd(PEt$_3$)$_2$, Pd(PCy$_3$)$_2$, Pd(dppb), Pd(dppe), Pd(dppp), Pd(BINAP) and the like. "Ph" represents phenyl, "Me" represents methyl, "Et" represents ethyl, "t-Bu" represents tert-butyl, "Cy" represents cyclohexyl, "dppb" represents 1,4-bis(diphenylphosphino)butane, "dppe" represents 1,2-bis(diphenylphosphino)ethane, "dppp" represents 1,3-bis(diphenylphosphino)propane and "BINAP" represents 2,2'-bis(diphenylphosphino)-1,1'-binaphthyl.

In the above-described polymerization reaction, if the above-described suitable catalyst is added in the presence of the generated organometal complex, a reaction occurs between X and/or Y and M in two molecules, to produce a direct bond between the repeating unit. By continuous occurrence of this reaction, a polymer of the present invention is obtained.

The regularity of the HT bond in a polymer obtained by the above-described polymerization reaction is believed to be determined depending on the generation selectivity of the above-described organometal compound and a difference in the reactivity thereof. Therefore, for obtaining a polymer having a sufficiently high proportion of the HT bond, it is preferable that at least one of (1) only one of the above-described organometal compounds (i) and (ii) is generated selectively, and (2) a difference in the reactivity in the reaction of the above-described organometal compound (i) or (ii) in the presence of the above-described catalyst is significant, is satisfied.

The present invention will be illustrated specifically referring to examples below, but the present invention is not limited to them al all.

EXAMPLE 1

(i) Synthesis of 2-bromo-4-hexylthiazole

To 40 mL of acetonitrile containing 10.0 g (54.3 mmol) of 2-amino-4-hexylthiazole (Helvetica Chemica Acta XXXII, Fasciculus I, 35 (1949)) dissolved therein, 8.39 mL (70.5 mmol) of t-butyl nitrite was added, and a suspension of 12.1 g (54.3 mmol) of copper(II) bromide in 20 mL of acetonitrile was added portion-wise while cooling with ice under an argon atmosphere and stirred for 2 hours. Then, the resultant reaction mixed liquid was poured into 100 ml of chloroform/hexane mixed liquid, and the precipitate was removed by filtration. The filtrate was washed with 100 ml of a 20 wt % hydrochloric acid aqueous solution three times, then, extracted with chloroform. The resultant extraction liquid was dried over anhydrous magnesium sulfate, then, concentrated under reduced pressure, and purified by silica gel column chromatography (development solvent:chloroform/hexane=1/1 (volumetric ratio)). Since a peak of a molecular weight of 248 containing one bromine atom was observed in the mass spectrum, it could be confirmed that the intended 2-bromo-4-hexylthiazole was obtained.

(ii) Synthesis of 2-bromo-4-hexyl-5-iodothiazole 4.07 g (16.4 mmol) of 2-bromo-4-hexylthiazole was dissolved in 8 mL of acetonitrile, and 32 mL of acetonitrile solution of 4.41 g (19.7 mmol) of N-iodosuccinimide was added under an argon gas atmosphere, and refluxed for 18 hours. Next, the resultant reaction mixed liquid was washed with a Na$_2$S$_2$O$_3$ aqueous solution, and the aqueous layer was extracted with chloroform and added to the organic layer. The organic layer was concentrated, and subjected to silica gel column chromatography (development solvent:chloroform/hexane=1/1 (volumetric ratio)) to take out red transparent liquid. Since a peak of a molecular weight of 373 containing one bromine atom was observed in the mass spectrum, it could be confirmed that the above-described red transparent liquid was the intended 2-bromo-4-hexyl-5-iodothiazole. The amount obtained was 4.80 g, and the yield was 78.3%.

The resultant red transparent liquid was identified as 2-bromo-4-hexyl-5-iodothiazole from the following data.

(1) $^1$H-NMR (ppm/300 MHz, CDCl$_3$) 0.89 (3H, t), 1.31 (6H, m), 1.66 (2H, m), 2.71 (2H, m)

(2) $^{13}$C-NMR (ppm/75 MHz, CDCl$_3$) 14.1, 22.6, 28.8, 29.0, 31.4, 31.5, 69.8, 138.9, 161.8

If 2-bromo-4-hexyl-5-iodothiazole is used as a monomer, a HT regioregular polymer can be synthesized at high yield.

EXAMPLE 2

(iii) Synthesis of 2-chloro-4-hexylthiazole

To 200 mL of acetonitrile was added 9.7 mL (81 mmol) of t-butyl nitrite and 8.75 g (65.1 mmol) of copper(II) chloride, and 10 mL of acetonitrile containing 10.0 g (54.3 mmol) of 2-amino-4-hexylthiazole (Helvetica Chemica Acta XXXII, Fasciculus I, 35 (1949)) dissolved therein was added to this portion-wise while cooling with ice under an argon atmosphere and the temperature thereof was returned to room temperature and the mixture was stirred for 2 hours. Then, the resultant reaction mixed liquid was poured into 100 ml of chloroform/hexane mixed liquid, and the precipitate was removed by filtration. The filtrate was washed with 100 ml of a 20 wt % hydrochloric acid aqueous solution three times, then, extracted with chloroform. The resultant extraction liquid was dried over anhydrous magnesium sulfate, then, concentrated under reduced pressure, and purified by silica gel column chromatography (development solvent:chloroform/hexane=1/1 (volumetric ratio)), to obtain the intended 2-chloro-4-hexylthiazole.

(iv) Synthesis of 2-chloro-4-hexyl-5-iodothiazole 5.30 g (26.0 mmol) of 2-chloro-4-hexylthiazole and 7.02 g (31.2 mmol) of N-iodosuccinimide were dissolved in 40 mL of acetonitrile, and stirred for 2 hours at 50° C. under argon gas purge. The resultant reaction mixed liquid was washed with a Na$_2$S$_2$O$_3$ aqueous solution, and the aqueous layer was extracted with chloroform and added to the organic layer. The organic layer was concentrated, and subjected to silica gel column chromatography (development solvent:chloroform/hexane=1/1 (volumetric ratio)) to take out red transparent liquid. Since a peak of a molecular weight of 330 containing one chlorine atom was observed in the mass spectrum (apparatus: HP-6890GC/HP-5973MSD, column: SGE BPX-5 (30 m×0.25 mm I.D.×025 µm), column temperature: 50° C. (5 minutes)→10° C./min.→350° C. (held for 5 minutes), injection port temperature: 280° C., carrier gas: He, 1.0 ml/min.), it could be confirmed that the above-described red transparent liquid was the intended 2-chloro-4-hexyl-5-iodothiazole. The amount obtained was 7.50 g, and the yield was 87.6%.

The resultant red transparent liquid was identified as 2-chloro-4-hexyl-5-iodothiazole from the following data.

(1) $^1$H-NMR (ppm/300 MHz, CDCl$_3$) 0.89 (3H, t), 1.31 (6H, m), 1.66 (2H, m), 2.69 (2H, m)

(2) $^{13}$C-NMR (ppm/75 MHz, CDCl$_3$) 14.0, 22.9, 29.1, 29.2, 31.78, 31.82, 68.4, 154.9, 160.5

EXAMPLE 3

(v) Synthesis of HT Regioregular Polythiazole

Under an argon gas atmosphere, 1.00 g (3.03 mmol) of 2-chloro-4-hexyl-5-iodothiazole was dissolved in 5 mL of tetrahydrofuran (THF), and cooled down to −78° C., then, 1.01 mL (3.03 mmol) of a 3.0 M methylmagnesium chloride THF solution was added dropwise, and stirred for 1 hour to obtain a reaction solution. A 5 mL of THF suspension of 0.082 g (0.15 mmol) of 1,3-diphenylphosphinopropanenickel (II) chloride (Ni(dppp)Cl$_2$) was poured into the reaction solution and stirred for 4.5 hours at 0° C., then, the reaction solution was added dropwise into 100 mL of methanol to find deposition of a precipitate. Thus obtained precipitate was dried under reduced pressure to obtain 328 mg (yield: 64.7%) of HT regioregular poly(4-hexylthiazole-2,5-diyl) (HT-PHTz) as a powder showing red purple color.

$^1$H-NMR (300 MHz) of thus obtained HT-PHTz was measured in a mixed solution of deuterated chloroform: trifluoroacetic acid (volumetric ratio 9:1). As a result, the ratio of the peak area of 3.0 to 3.3 ppm (CH$_2$ proton adjacent to thiazole ring having HT structure) to the peak area of 2.7 to 3.0 ppm (CH$_2$ proton adjacent to thiazole ring having non-HT structure) taught that the proportion of the total number of direct bonds forming the HT bond was 92% with respect to the total number of direct bonds between repeating units of the following formula (IVa):

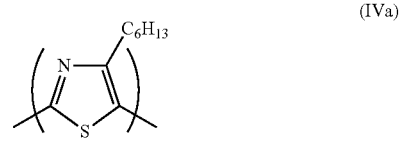

(IVa)

derived from a plurality of heterocyclic compounds of the above-described formula (I) contained in the HT-PHTz.

Peaks were observed at an interval of the mass of the repeating unit by MALDI-TOFMS measurement of thus obtained HT-PHTz, to confirm a structure in which the end of the HT-PHTz molecule was a hydrogen atom, hydroxyl group or chlorine atom, and 7 to 29 repeating units of the above-described formula (IVa) were connected serially.

Here, 1,4-diphenyl-1,3-butadiene (reagent manufactured by Lancaster) was used as a matrix for MALDI mass analysis. Regarding the mixing ratio of the matrix for MALDI mass analysis and the analysis subject sample, THF solutions prepared at a concentration of 20 mg/mL for the matrix for MALDI mass analysis and a concentration of 10 mg/mL for the analysis subject sample, respectively, were mixed at 5:1 (volumetric ratio), referring to J. Am. Soc. Mass Spectrom. 1996, 7, 11-24 and Rapid Commun. Mass Spectrom 2001, 15, 675-678. The mixed solution of the matrix for MALDI mass analysis and the analysis subject sample substance was poured in an amount of 1.5 µl by a micropipetter and allowed to adhere onto a target for MALDI mass analysis, and the target was inserted into Reflex III type MALDI mass analysis apparatus manufactured by Bruker Daltonics K.K. Thereafter, measurement was performed in positive-ionization mode with laser shot 1000-times accumulation at an accelerating voltage of 27.5 kV.

COMPARATIVE EXAMPLE 1

(iv) Synthesis of Polythiazole

Under an argon gas atmosphere, a solution of 0.50 g (1.59 mmol) of 2,5-dibromo-4-hexylthiazole (can be synthesized by a method described in J. Chem. Soc. PerkinTrans. 1, 1981, p. 2335-2339), 0.925 g (3.36 mmol) of bis(1,5-cyclooctadiene)nickel(0) (Wako Pure Chemical Industries Ltd.) and 0.525 g (3.36 mmol) of bipyridine (Wako Pure Chemical Industries Ltd.) in THF (10 mL) was refluxed under an argon gas atmosphere for 90 minutes, and thus obtained reaction mixture was cooled, then, added dropwise into 50 mL of methanol to find deposition of a precipitate. This precipitate was washed with methanol and dried under reduced pressure, to obtain 87 mg (yield: 34%) of regiorandom poly(4-hexylthiazole2,5-diyl) (RR-PHTz) as a powder showing red brown color.

$^1$H-NMR (300 MHz) of thus obtained RR-PHTz was measured in a mixed solution of deuterated chloroform: trifluoroacetic acid (volumetric ratio 9:1). As a result, the ratio of the peak area of 3.0 to 3.3 ppm ($CH_2$ proton adjacent to thiazole ring having HT structure) to the peak area of 2.7 to 3.0 ppm ($CH_2$ proton adjacent to thiazole ring having non-HT structure) taught that the proportion of the total number of direct bonds forming the HT bond was 40% with respect to the total number of direct bonds between repeating units of the above-described formula (I)

REFERENCE EXAMPLE 1

Powder X-ray analysis was carried out to find that the distance between main chain planes in the solid state of HT-PHTz was 3.60 Å. This value is smaller than 3.80 Å as an inter-planar distance of poly(3-hexylthiophene) having a HT bond proportion of over 98% which is a typical polymer manifesting easy flow of electricity (see, J. Am. Chem. Soc. 115, 4910 (1993)). Therefore, HT-PHTz is expected to show excellent packing between molecules, have near π orbital between molecules, and have high moving efficiency of charges.

REFERENCE EXAMPLE 2

Using a mixed solvent of chloroform: trifluoroacetic acid (volumetric ratio 10:1), a solution of the HT-PHTz (the total concentration of all repeating units: $1\times10^{-4}$ mol/L) and a solution of the RR-PHTz (the total concentration of all repeating units: $1\times10^{-4}$ mol/L) were prepared, respectively, and UV absorption spectra thereof were observed by an ultraviolet visible spectrophotometer (trade name: V-530, manufactured by JASCO Corporation). The maximum absorption wavelength (vHT-PHTz) of the HT-PHTz solution was 499 nm, and the maximum absorption wavelength (vRR-PHTz) of the RR-PHTz solution was 453 nm.

It is understood that HT-PHTz has an absorption maximum at the longer wavelength side than RR-PHTz, and HT-PHTz has higher flatness, thus, shows good conjugation connection, the energy difference between HOMO level and LUMO level is smaller, and a light of weaker energy can be absorbed by HT-PHTz. Therefore, HT-PHTz is expected to show better packing between molecules, have nearer it orbital between molecules and show higher charge moving efficiency.

The heterocyclic compound of the present invention can be used to synthesize a HT regioregular polymer having as a repeating unit a 5-membered ring of asymmetric ring structure. Usually, the HT regioregular polymer is obtained with high yield.

It is estimated that in the polymer of the present invention, the orientations of bonds between repeating units of the above-described formula (IV) are substantially controlled to a constant direction, thus, repulsion between atoms constituting side chains of adjacent repeating units is lowered, to increase flatness thereof. This polymer is guessed to show high mobility since the conjugation length increases and the packing property between molecules is improved because of such structural features. The polymer of the present invention has high HT selectivity, manifests excellent practical utility, and usually has sufficiently high molecular weight.

Further, by applying the production method of the present invention, the polymer of the present invention can be synthesized easily in a short process.

The invention claimed is:

1. A polymer having a repeating unit of the following formula (IV):

wherein $R^3$ represents a substituent; the combination of $A^1$ and $A^2$ is a combination of —S— and —N=, a combination of —O— and —N=, a combination of —Se— and —N=, or a combination of —S— and —Si($R^2$)=, wherein $R^2$ represents a hydrogen atom or an optionally substituted hydrocarbon group; and one of two linkages each represented by a solid line and a dashed line is a single bond, while the other is a double bond and wherein (A) the polymer has a structure containing consecutively connected 7 or more of the repeating units (Condition A), and (B) the proportion of the total number of direct bonds forming a head to tail (HT) bond with respect to the total number of direct bonds between the plurality of repeating units contained in the polymer is 60% or more (Condition B).

2. The polymer according to claim 1, wherein the polymer further has a repeating unit other than the repeating unit of the above-described formula (IV), and the proportion the total number of repeating units of the above-described formula (IV) with respect to the total number of all repeating units contained in the polymer is 80% or more and less than 100%.

3. A method of producing the polymer described in claim 1, which comprises condensing a heterocyclic compound of the following formula (V):

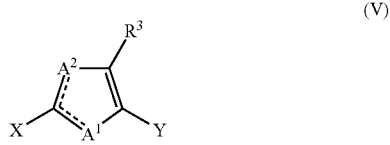

wherein $R^3$, $A^1$, $A^2$ and solid lines and dashed lines represent the same meanings as described above, and wherein X and Y are different from each other and represent a halogen atom selected from the group consisting of a chlorine atom, a bromine atom, and an iodine atom, or $CF_3SO_3^-$, $CH_3SO_3^-$, $C_6H_5SO_3^-$, or $CH_3C_6H_4SO_3^-$.

* * * * *